United States Patent [19]

Ridoux

[11] Patent Number: 4,979,989
[45] Date of Patent: Dec. 25, 1990

[54] ALGINATE-TYPE POWDERED COMPOSITION FOR DENTAL IMPRESSIONS

[75] Inventor: Claude Ridoux, Isle Sur La Sorgue, France

[73] Assignee: Societe Anonyme Sanofi, Paris, France

[21] Appl. No.: 318,262

[22] Filed: Mar. 3, 1989

[30] Foreign Application Priority Data

Mar. 3, 1988 [FR] France ................................ 88 02723

[51] Int. Cl.$^5$ .......................... A61K 9/00; C08L 1/08; B28B 7/00
[52] U.S. Cl. .................................... 106/35; 106/38.23; 106/205; 106/209; 427/213.3; 427/213.35; 433/214; 523/109
[58] Field of Search ............. 523/109; 433/214, 217.1; 106/35, 38.23, 205, 209; 427/220, 213.3, 213.35

[56] References Cited

U.S. PATENT DOCUMENTS

| 1,920,857 | 8/1933 | Harrison | 106/35 |
| 4,161,411 | 7/1979 | Sell et al. | 106/100 |
| 4,248,736 | 2/1981 | Fuchigami et al. | 502/402 |
| 4,316,811 | 2/1982 | Burns et al. | 427/220 |
| 4,394,172 | 7/1983 | Scheuble et al. | |
| 4,543,372 | 9/1985 | Watanabe et al. | 106/206 |
| 4,689,079 | 8/1987 | Buma et al. | |
| 4,689,297 | 8/1987 | Good et al. | 252/DIG. 12 |
| 4,778,832 | 10/1988 | Futami et al. | 523/109 |
| 4,911,759 | 3/1990 | Ohi et al. | 106/35 |

FOREIGN PATENT DOCUMENTS 2572931 5/1986 France .
82/00650 3/1982 World Int. Prop. O. .

Primary Examiner—Paul Lieberman
Assistant Examiner—John Boyd
Attorney, Agent, or Firm—Foley & Lardner, Schwartz, Jeffery, Schwaab, Mack, Blumenthal & Evans

[57] ABSTRACT

A powdered composition for dental impressions, comprising a water-soluble alginate, a gelling agent, a gelling regulator and fillers coated with a hydrolyzed gelatin.

6 Claims, No Drawings

ALGINATE-TYPE POWDERED COMPOSITION FOR DENTAL IMPRESSIONS

The present invention relates to an alginate-type powdered composition for the preparation of dental impressions, whose wettability, fluidity and pulverulence characteristics are improved by comparison with the conventional materials.

Dental impressions are commonly made using materials composed essentially of at least one water-soluble alginate, a gelling agent for alginate solutions, a gelling regulator and powdered mineral fillers.

The water-soluble alginate can be an alkali metal alginate, an ammonium alginate, an alkanolamine alginate or a mixture thereof; the gelling agent can be a metal salt: a metal salt of a fatty acid, such as a calcium oleate, a zinc laurate or an iron stearate, or a metal salt of a mineral acid, such as an iron or zinc sulfate or, preferably, a hydrated calcium sulfate; the gelling regulator can be selected from alkali metal phosphates, pyrophosphates, silicates, carbonates or citrates and mixtures thereof. The fillers which are introduced into the mixture to improve its consistency and its strength are generally diatomaceous earths, silica, talc, perlite or mixtures thereof.

The powdered mixture of the components is mixed with water by the practitioner just before the impression is taken, which is done by using an impression tray to apply the resulting paste to that area of the patient's jaw whose morphology is to be recorded in order to prepare a prosthesis or make a model; when the paste has gelled, the elasticity of the impression enables it to be removed from the mouth and cast in plaster. This plaster model is subsequently used to prepare a prosthesis or to carry out an orthodontic study.

Reference may be made to the book of E. W. SKINNER and R. W. PHILIPS—Science des matériaux dentaires (Science of dental materials)—published by Julien PRELAT, Paris, which gives the typical composition of the alginate-type impression materials.

It has also been proposed to add various compounds to these conventional compositions in order to improve the properties of the material, and in particular to improve the malleability of the paste by adding plasticizers such as alcohols or mineral or vegetable oils, or to improve the precision of the impression, for example by adding fluorides, preferably with alkali metal oxides or hydroxides so as also to improve the stability of the powder and the strength of the gel, as described in U.S. Pat. No. 3,291,668, or by adding polyacrylamide to the mixture, as described in European Pat. No. 198131, or by adding polymers to the paste before it is used, as described in U.S. Pat. No. 3,620,778.

Colors, flavorings and preservatives may also be introduced into the material.

More recently, compositions for dental impressions have been proposed which release only a small amount of dust when used. In actual fact, it is common for the mixture to become heterogeneous during storage, the densest constituents tending to settle out at the bottom of the box, and the practitioner is accustomed to shaking the container before removing the amount of powder required to prepare an impression paste, which causes fine particles to be dispersed into the atmosphere when the box is opened; this is undoubtedly unpleasant for the people present in the room, and can also be toxic.

Thus, European patent application No. 0058203 describes a powdered composition for dental impressions in which at least some of the constituents have been coated with a coating agent which is easy to wet, disperse or dissolve in water; the following are mentioned among these coating agents: dispersing polymers such as xanthan gum, alkali metal polyalginates and cellulose ethers and esters, and surface-active polymers such as polyalkylene glycols, or even low-molecular weight molecules such as polyols, glycerol esters, alkanolamines and laurylsulfates.

In Japanese patent application No. 58-98021, it is provided to coat the particles of powder with a nonionic surfactant and a hydrophobic liquid with a vapor pressure of less than 3.15 mm Hg at 20° C., whereas in French patent application No. 2 553 999, polyvinylpyrrolidone is added to the powder coated in this way in order to improve the storage stability of the product and the surface condition of the plaster cast which is to be prepared from the alginate impression.

In European patent application No. 0 217 270, it is provided to introduce an isoparaffin, such as 2,2,4,4,6,6,8-heptamethylnonane or 2,2,4,4,6,6,8,8,10-nonamethylundecane into a conventional mixture in order to reduce the amount of volatile dust released.

Finally, in German patent application No. 35 11 721, it is provided to granulate the whole of the mixture with a polymer such as hydroxypropyl cellulose or polyvinylpyrrolidone.

The materials according to the present invention do not release dust when used; furthermore, they have good flow properties, are not sticky, as the materials treated with liquids can be, and are readily wetted by water, in contrast to the materials treated with hydrophobic compounds or granules, which makes the paste easier to prepare and homogenize.

According to the present invention, the mineral fillers introduced into an alginate-type material of conventional composition, for dental impressions, are coated beforehand with a water-soluble hydrolyzed gelatin.

The fillers are coated with a film of hydrolyzed gelatin by atomization, immersion or spraying of the powdered fillers with an aqueous solution of hydrolyzed gelatin in a coating turbine, a planetary mixer, a granulating mixer or a sieve granulator or in a fluidized bed granulator, for example in an atomizing granulator, and the particles which have been coated in this way are then dried in a stream of hot air, at a temperature of between 20° C. and 80° C., in an appropriate apparatus, such as a drying tunnel, or in the apparatus in which the coating was carried out if this was a coating turbine or a fluidized apparatus.

The film of hydrolyzed gelatin represents from 1 to 10% by weight of the fillers and more particularly from 3 to 6%.

The hydrolyzed gelatin is prepared by the action of an acid, a base, the heat or an enzyme on a conventional gelatin resulting from acid or alkaline hydrolysis of the collagen present in the bones, skin or tendons of cattle, pigs or sheep. The starting gelatin generally has a molecular weight between 60,000 and 300,000, whereas the hydrolyzed gelatin has an average molecular weight between 500 and 30,000 and preferably between 5,000 and 10,000. This hydrolyzed gelatin is soluble in water at room temperature, i.e. at about 20° C., and has no gel strength which can be measured under the conditions defined by "British Standards", at a concentration of 6.67% (w/v) in water after 17 hours at 10° C.

The processes for hydrolyzing gelatin are well known to those skilled in the art; reference may be made in particular to French patent application No. 2 099 777 and U.S. Pat. No. 4,130,555 or to the documents published by NOVO (Denmark), especially to NOVO Enzyme Information ref. No. 163b.

Hydrolyzed gelatins are commercially available; the gelatin having the reference SPG or the reference DSF, marketed by MERO ROUSSELOT SATIA (France) which is now SANOFI BIO INDUSTRIE, and the gelatin called Crotein A, marketed by CRODA (Great Britain), may be mentioned in particular.

Examples of how the invention is put into practice are described below and the results obtained are compared with those for compositions not having the characteristics of the invention.

EXAMPLE 1

The filler used is a diatomaceous earth called Clarcel; it is coated with the hydrolyzed gelatin marketed by the company MERO ROUSSELOT SATIA under the reference SPG.

400 g of Clarcel and 320 ml of a 5% (w/v) aqueous solution of gelatin SPG (MERO ROUSSELOT SATIA) are introduced into a Uniglatt fluidized bed granulator marketed by Glatt (FRG). With the mass of powder suspended in air, the solution of binder is atomized under pressure onto the fluid bed of powder.

This produces a granular powder of coated Clarcel containing 4% of gelatin, which flows freely and whose characteristics are compared in Table I with those of the starting material.

TABLE I

| | Clarcel | Coated Clarcel |
|---|---|---|
| Bulk volume: | 4 m³/kg | 5.36 m³/kg |
| Bulk density: | 0.25 kg/m³ | 0.186 kg/m³ |
| Particle size distribution: | | |
| >500 μm | 0.16% | 1.4% |
| >250 μm | 1.1% | 10.64% |
| >100 μm | 24.2% | 61.54% |
| >40 μm | 46.62% | 23.04% |
| <40 μm | 27.92% | 3.38% |

The impression composition is prepared by dry mixing the following products in a high-speed blade mixer marketed by Lödige :

| | |
|---|---|
| Coated Clarcel | 64.2 g |
| Alginate from laminar alga, potassium salt | 15.1 g |
| Calcium sulfate dihydrate | 1 g |
| Potassium fluorotitanate | 4.6 g |

The composition is then boxed. When the box is opened after shaking, no powder is released into the air.

10 g of this material are then mixed with 21 ml of water, using a spatula, in a small semi-rigid plastic bowl; the powder is wetted very quickly and the water is easily incorporated; the paste is ready in 30 seconds and sets after 3 minutes at 20° C.

The powdered mixture prepared under the same conditions but with uncoated Clarcel releases particles into the air after the box has been shaken, and the paste is more difficult to prepare; the powder is wetted less well and it takes longer to incorporate all the water into the paste.

The two materials give the same gelling time and the gel obtained in both cases makes it possible to reproduce very fine details of the order of 35 μm.

Another powdered mixture was prepared under the same conditions but with Clarcel coated with a film of a conventional gelatin having a gel strength of 80 blooms, measured according to British Standards. The shaken mixture does not release dust but this composition cannot be used to prepare a paste suitable for taking impressions: the particles are difficult to wet and cannot be crushed with a spatula, and the final product is a granular gel.

EXAMPLE 2

The coated filler is the same as in Example 1 but it is used to prepare an impression powder to be applied as a fluid paste with a distributing syringe.

The mixture consists of:

| | |
|---|---|
| Granular Clarcel | 63 g |
| Alginate from laminar alga, potassium salt | 6.5 g |
| Cloustonii alginate, sodium salt | 6.5 g |
| Calcium sulfate | 3.7 g |
| Potassium fluorotitanate | 2 g |
| Magnesium oxide | 1 g |

This mixture does not release dust when shaken.

A fluid paste is prepared with 7 g of powdered mixture and 21 ml of water.

This paste gels in 4 minutes at 20° C. The mixture prepared with conventional Clarcel releases dust and it is more difficult to prepare a homogeneous fluid paste with it than with the mixture according to the invention. The setting time, the fineness of the gel obtained and the possibility of reproducing fine details are not reduced with the material according to the invention.

What is claimed is:

1. In a powdered dental impression composition, comprising at least one water-soluble alginate, a gelling agent, a gelling regulator and mineral fillers, the improvement wherein said mineral fillers are coated with from about 1% to 10% by weight of a hydrolyzed gelatin.

2. The powdered composition according to claim 1, wherein said mineral fillers are coated with from about 3% to 6% by weight of said hydrolyzed gelatin.

3. The powdered composition according to claim 1, wherein said hydrolyzed gelatin has an average molecular weight of about 500 to 30,000.

4. The powdered composition according to claim 3, wherein said hydrolyzed gelatin has an average molecular weight of about 5,000 to 10,000.

5. The powdered composition according to claim 1, wherein said hydrolyzed gelatin is soluble in water at room temperature and has substantially no gel strength at a concentration of 6.67% weight per volume in water after 17 hours at 10° C.

6. A method of manufacturing a powdered dental impression composition comprising at least one water-soluble alginate, a gelling agent, a gelling regulator and mineral fillers, said method comprising:
(a) coating said mineral fillers with from about 1% to 10% by weight of a hydrolyzed gelatin in a fluidized bed reactor; and
(b) combining resultant coated mineral fillers with said water-soluble alginate, said gelling agent and said gelling regulator.

* * * * *